US00PP32515P2

(12) United States Plant Patent
Mathey

(10) Patent No.: US PP32,515 P2
(45) Date of Patent: Nov. 24, 2020

(54) ***LAGERSTROEMIA* PLANT NAMED 'SMNLCIBF'**

(50) Latin Name: *Lagerstroemia indica*
Varietal Denomination: SMNLCIBF

(71) Applicant: Spring Meadow Nursery, Inc., Grand Haven, MI (US)

(72) Inventor: Megan M Mathey, Holland, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/602,600

(22) Filed: Nov. 4, 2019

(51) Int. Cl.
*A01H 5/02* (2018.01)
*A01H 6/00* (2018.01)

(52) U.S. Cl.
USPC ..... Plt./252

(58) Field of Classification Search
USPC ..... Plt./252
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Lagerstroemia* plant named 'SMNLCIBF' is disclosed, characterized by vibrant red flowers, and greyed-purple foliage. Plants are compact and freely branching with good resistance to powdery mildew. The new variety is a *Lagerstroemia*, normally used for outdoor ornamental purposes.

2 Drawing Sheets

Latin name of the genus and species: *Lagerstroemia indica.*

Variety denomination: 'SMNLCIBF'.

BACKGROUND OF THE INVENTION

The new *Lagerstroemia* cultivar is a product of a planned breeding program conducted by the inventor, Megan Mathey, in Grand Haven, Mich. The objective of the breeding program was to develop new forms and colors. The open pollination resulting in this new variety was made during the Summer of 2016.

The seed parent is the commercial variety referred to as *Lagerstroemia* 'Coral Magic', U.S. Plant Pat. No. 23,922. The pollen parent is unidentified. The new variety was selected in Summer 2017 by the inventor in a group of seedlings resulting from the 2016 open pollination, in a nursery in Grand Haven, Mich. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar was performed by softwood cuttings. This was first performed at the same nursery in Grand Haven, Mich. during Summer 2017, and has shown that the unique features of this cultivar are stable and reproduced true to type in multiple successive generations.

SUMMARY OF THE INVENTION

The cultivar 'SMNLCIBF' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNLCIBF'. These characteristics in combination distinguish 'SMNLCIBF' as a new and distinct *Lagerstroemia* cultivar:

1. Vibrant red blooms.
2. Greyed-Purple foliage.
3. Good branching.
4. Good powdery mildew resistance.

PARENT COMPARISON

Plants of the new cultivar 'SMNLCIBF' are similar to plants of the seed parent, *Lagerstroemia* 'Coral Magic', U.S. Plant Pat. No. 23,922, in most horticultural characteristics; however, plants of the new cultivar 'SMNLCIBF' differ in the following;

1. The new variety has greyed-purple foliage, while the seed parent has green foliage.
2. The new variety has red flowers, while the seed parent has coral-pink flowers.

COMMERCIAL COMPARISON

Plants of the new cultivar 'SMNLCIBF' are comparable to the commercial variety *Lagerstroemia* 'PIILAG-IX', U.S. Plant Pat. No. 29,325. The two *Lagerstroemia* varieties are similar in most horticultural characteristics; however, the new variety 'SMNLCIBF' differs in the following;

1. The new variety has vibrant red blooms, while this comparator has darker red blooms.
2. New variety has larger flower panicles than this comparator.
3. New variety has twisting leaves, while this comparator has flat leaves.

BRIEF DESCRIPTION OF THE PHOTOGRAPHS

Figure 1:
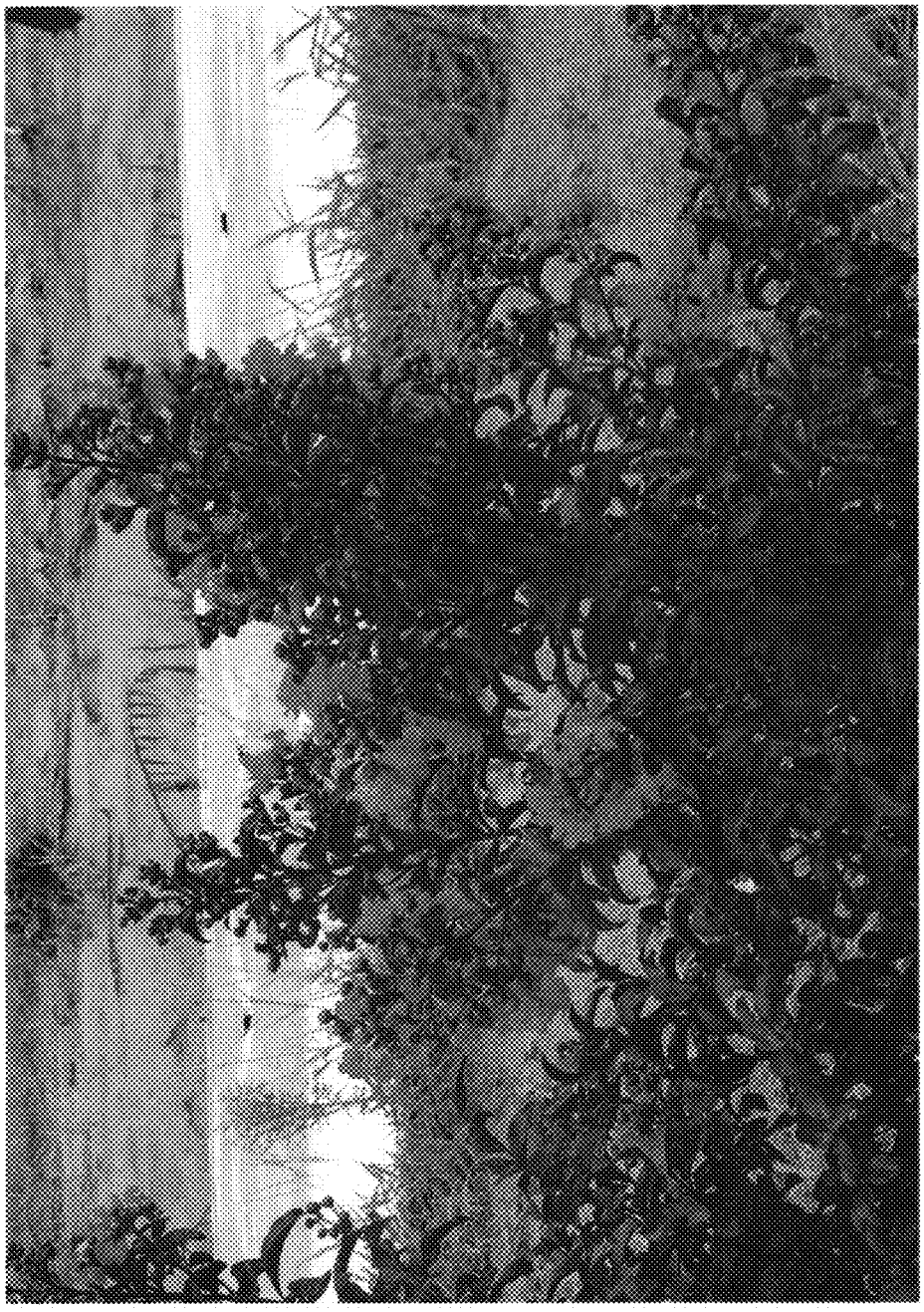

The accompanying photograph in FIG. 1 illustrates a typical flowering plant of 'SMNLCIBF' grown outdoors.

Figure 2:
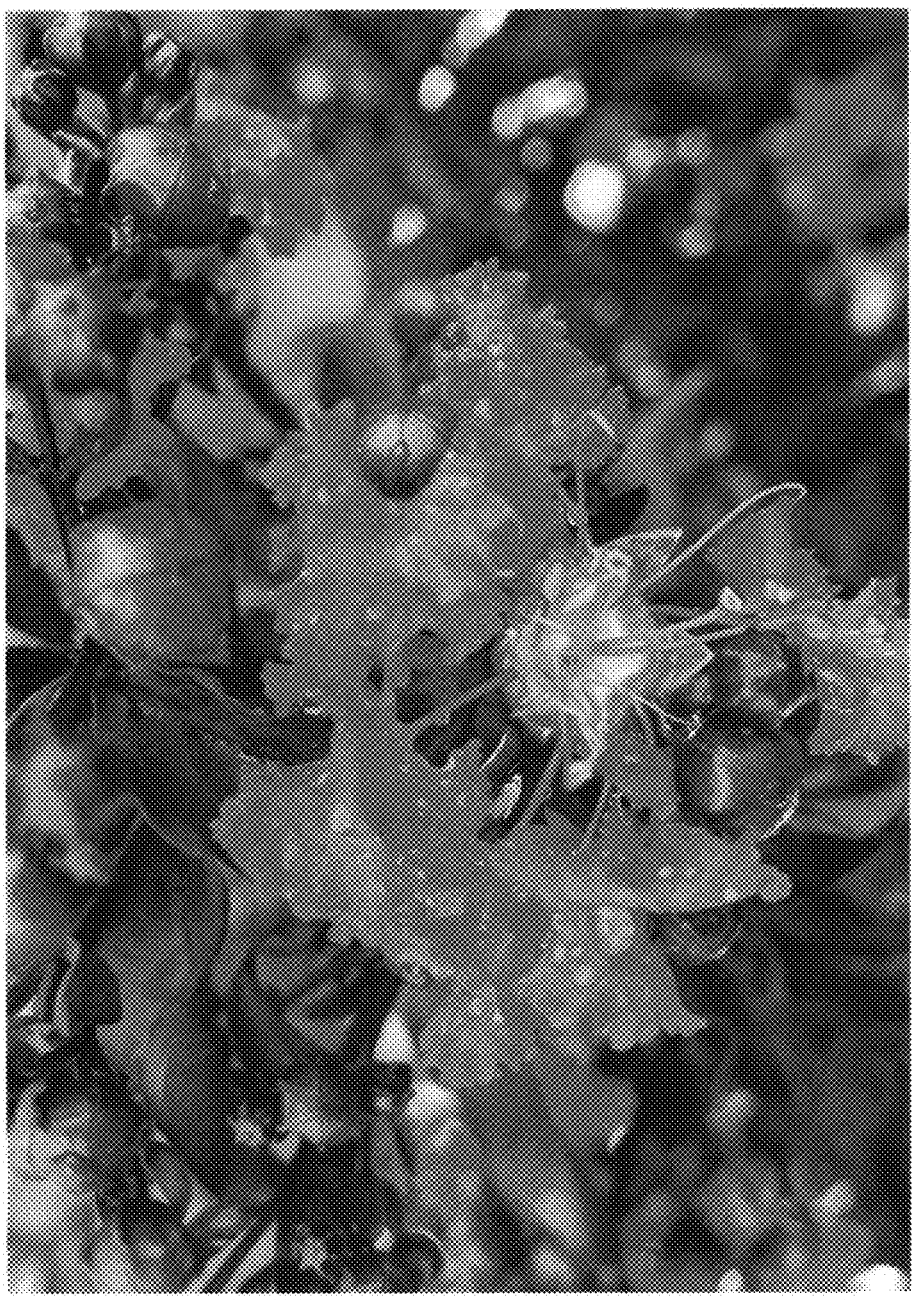

FIG. 2 illustrates a close-up view of the inflorescence. Age of the plant photographed is approximately 2-3 years old from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNLCIBF' plants grown in a poly house during August 2017, in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'SMNLCIBF'.

PROPAGATION

Type of propagation typically used: Softwood cuttings.
Time to initiate roots: 21 days at 18-27° C.
Time to produce a rooted cutting: 1-2 months at 18-27° C.
Root description: Thin fibrous, dense, moderate branching. White in color, not accurately measured with R.H.S. Chart.

PLANT

Age of plant described: 2-3 years old from a rooted cutting.
Container size: 3 gallon container.
Overall plant shape: Compact, rounded.
Growth habit: Upright and outward.
Plant spread: 60 cm.
Plant height: 111 cm.
Plant vigor: Good.
Length of primary lateral branches: 34 cm.
Diameter of lateral branches: 4 mm.
Quantity of lateral branches: 18.
Stem:
- *Color*.—New growth: RHS Greyed-Purple 187B. Old growth: RHS Brown N200A.
- *Shape*.—Square.
- *Strength*.—Strong.
- *Aspect angle*.—15-45°.
- *Pubescence*.—None. Old growth woody.

Internode length: Average 12 cm.

FOLIAGE

Leaf:
- *Arrangement*.—Sub-opposite, single.
- *Average length*.—5.5 cm.
- *Average width*.—2.25 cm.
- *Shape of blade*.—Elliptic, folds in half.
- *Apex*.—Acute.
- *Base*.—Cuneate.
- *Margin*.—Entire, and wavy.
- *Texture of top surface*.—Smooth.
- *Texture of bottom surface*.—Ribbed.
- *Color*.—Young foliage upper side: RHS Greyed-Purple N186A. Young foliage under side: RHS Brown 201A. Mature foliage upper side: RHS Greyed-Purple N186A. Mature foliage under side: RHS Brown 201A.
- *Venation*.—Type: Pinnate. Venation color upper side: RHS Greyed-Red N187A. Venation color under side: RHS Greyed-Purple 183C.
- *Petiole*.—Length: 2 mm. Diameter: 1.5 mm. Texture, upper side: Smooth. Texture, under side: Smooth. Color, upper side: RHS Greyed-Purple 187A. Color, under side: RHS Greyed-Purple 187A.

FLOWER

Natural flowering season: Summer through Fall.
Arrangement: Panicles at terminal ends of branches.
Inflorescence form: Panicle.
Flowers per inflorescence: 2 to 50.
Flowers per lateral stem: 2 to 50.
Inflorescence size:
- *Width*.—17 cm.
- *Height*.—20 cm.

Individual flowers:
- *Shape*.—Whorled, rotate of 6 freely attached petals.
- *Habit*.—Whorled upward and outward.
- *Diameter*.—2 cm.
- *Length*.—4 cm.
- *Persistence*.—Self-cleaning.
- *Fragrance*.—Very light earthy.

Petals:
- *Arrangement*.—Whorled.
- *Appearance*.—Delicate, undulate, dimensional.
- *Number*.—6.
- *Shape*.—Loosely edged and undulate orbit shape.
- *Margin*.—Loose, undulate.
- *Tip shape*.—Rounded.
- *Base shape*.—Rounded.
- *Length*.—1.5 cm.
- *Width*.—1.5 cm.
- *Texture*.—Upper: Soft, smooth, delicate. Lower: Soft, smooth, delicate.
- *Color*.—When opening: Upper surface: RHS Red 53C. Under surface: RHS Red 53C. Fully opened: Upper surface: RHS Red 53C. Under surface: RHS Red 53C.

Bud:
- *Shape*.—Spherical.
- *Length*.—6 mm.
- *Diameter*.—8 mm.
- *Color*.—RHS Greyed-Purple 187B.
- *Prominence*.—Medium.

Sepals:
- *Appearance*.—Smooth, glossy, fused.
- *Arrangement*.—Unguiculate.
- *Shape*.—Narrowly triangular.
- *Tip shape*.—Acute.
- *Base shape*.—Obtuse.
- *Margin*.—Entire.
- *Quantity per flower*.—6.
- *Length*.—5 mm.
- *Width*.—4 mm.
- *Texture*.—Upper: Smooth, coriaceous, rugose. Lower: Smooth.

*Color*.—Upper: RHS Greyed-Purple 185A. Lower: RHS Greyed-Purple 185C.

Calyx:

*Shape*.—Unguiculate.

*Length*.—6 cm.

*Diameter*.—1 cm.

Pedicel:

*Length*.—5 mm.

*Diameter*.—1 cm.

*Angle*.—45°.

*Texture*.—Smooth.

*Color*.—RHS Greyed-Purple 187B.

*Strength*.—Good.

Peduncle:

*Length*.—7 mm.

*Diameter*.—2 mm.

*Texture*.—Smooth.

*Color*.—RHS Greyed-Purple 187B.

*Strength*.—Good.

*Angle*.—About 45°.

REPRODUCTIVE ORGANS

Stamens:

*Number*.—About 29.

*Filament length*.—1 cm.

*Filament color*.—RHS Red-Purple 70D, with White 155B at base.

Anthers:

*Shape*.—Linear.

*Length*.—1 mm.

*Color*.—RHS Yellow 9A.

*Pollen*.—Amount: Some. Color: RHS Yellow 9A.

Pistil:

*Number*.—1.

*Length*.—2 cm.

*Style*.—Length: 1.8 cm. Color: RHS Greyed-Purple 184D.

Stigma:

*Shape*.—Globe.

*Color*.—RHS Black 202A.

*Ovary color*.—RHS Yellow 11B.

OTHER CHARACTERISTICS

Fruits and seeds: Not observed to date.

Disease/pest resistance: Good powdery mildew resistance (*Erysiphe lagerstroemia*). Neither resistance nor susceptibility to other normal diseases and pests of *Lagerstroemia* observed.

Temperature range: Observed to tolerate a temperature range from −28° C. to 35° C. Root hardy to −28 C, top of the plant does die back to the ground.

What is claimed is:

1. A new and distinct cultivar of *Lagerstroemia* plant named 'SMNLCIBF' as herein illustrated and described.

* * * * *